United States Patent
Cui et al.

(10) Patent No.: US 10,655,160 B2
(45) Date of Patent: May 19, 2020

(54) FORMALDEHYDE GRAPHENE SENSOR

(71) Applicant: Regents of the University of Minnesota, Mineapolis, MN (US)

(72) Inventors: Tianhong Cui, Vadnais Heights, MN (US); Shota Sando, Minneapolis, MN (US)

(73) Assignee: Regents of the University of Minnesota, Mineapolis, MN (US)

( * ) Notice: Subject to any disclaimer, the term of this patent is extended or adjusted under 35 U.S.C. 154(b) by 674 days.

(21) Appl. No.: 14/840,694

(22) Filed: Aug. 31, 2015

(65) Prior Publication Data

US 2017/0059507 A1    Mar. 2, 2017

(51) Int. Cl.
*C12Q 1/32*    (2006.01)

(52) U.S. Cl.
CPC ..................... *C12Q 1/32* (2013.01)

(58) Field of Classification Search
CPC ........................................... C12Q 1/32
See application file for complete search history.

(56) References Cited

U.S. PATENT DOCUMENTS

| | | | |
|---|---|---|---|
| 2009/0008248 A1* | 1/2009 | Shimomura | B82Y 5/00 204/403.14 |
| 2010/0175991 A1 | 7/2010 | Shimomura et al. | |
| 2013/0018599 A1 | 1/2013 | Peng | |
| 2013/0053665 A1* | 2/2013 | Hughes | A61B 5/14532 600/347 |

FOREIGN PATENT DOCUMENTS

| | | |
|---|---|---|
| WO | 9919507 | 4/1999 |
| WO | 1999019507 A1 | 4/1999 |
| WO | 2010011798 A2 | 1/2010 |
| WO | 2010011798 A2 | 1/2012 |

OTHER PUBLICATIONS

Majidi et al., "Adsorption of formaldehyde on graphene and graphyne", Jan. 25, 2014, Physica E, 59, pp. 169-173.*
Marzuki et al., "Development of Electrochemical Biosensor for Formaldehyde Determination Based on Immobilized Enzyme", 2012, International Journal of Electrochemical Science, 7, pp. 6070-6083.*
Schedin et al., "Detection of individual gas molecules adsorbed on graphene", Nature Materials, vol. 6, All Pages. (Year: 2007).*
Nanowerk, "Carbon nanotubes—what they are, how they are made, what they are used for", https://www.nanowerk.com/nanotechnology/introduction/introduction_to_nanotechnology_22.php, 2018, All Pages. (Year: 2018).*
www.brenda-enzymes.org/enzyme.php?ecno=1.2.1.46. (Information on EC 1.2.1.46—Formaldehyde dehydrogenase).

(Continued)

*Primary Examiner* — Jeffrey T Barton
*Assistant Examiner* — Daniel P Malley, Jr.
(74) *Attorney, Agent, or Firm* — Shumaker & Sieffert, P.A.

(57) ABSTRACT

A formaldehyde electrochemical sensor employing a formaldehyde sensitive assembly of formaldehyde dehydrogenase attached to graphene in fluid communication with a source of $NAD^+$, and a method of measuring formaldehyde utilizing the sensor.

18 Claims, 9 Drawing Sheets

(56) References Cited

OTHER PUBLICATIONS

Chung, Po-Ren et al., "Formaldehyde Gas Senseors: A Review" www.mdpi.com/journal/sensors, Sensors, Feb. 27, 2013, pp. 4469-4484.

Marzuki, Nur Indang et al., "Development of Electrochemical Biosensor for Formaldehyde Determination Based on Immobilized Enzyme", www.lectrochemsci.org, Internationa Juernal of Electrochemical Science, Apr. 26, 2012, pp. 6071-6083.

Wang, Mingwei, "Formaldehyde Biosensor with Formaldehyde Dehydrogenase Adsorped on Carbon Electrode Modiiiiiiiified with Polypyrrole and Carbon Nanotube", Scientific Research, Engineering, 2012, pp. 135-138.

Kudo, Hiroyuki et al, "Biochemical Gas Sensor (bio-sniffer) for Ultrahigh-Sensitive Gaseous Formaldehyde Monitoring", Biosensors and Bioelectronics 26, Elsevier, Mar. 19, 2010, pp. 854-858.

Achmann, S. et al., "Direct Detection of Formaldehyde in Air by a Novel NAD+- and Glutathione-Independent Formaldehyde Dehydrogenase-Based Biosensor" Talanta, Elsevier, Jul. 30, 2007, pp. 786-791.

Basu, S. et al., "Recent Developments on Graphene and Graphene Oxide Based Solid State Gas Sensors", Sensors and Actuators B: Chemical, Elsevier, Mar. 12, 2012, pp. 1-21.

Schedin, F., "Detection of Individual Gas Molecules Adsorbed on Graphene", Nature Materials, Nature Publishing Group, vol. 6, Jul. 29, 2007, pp. 652-655.

Zhang, Bo et al., "An Ultrasensitive and low-cost graphene sensor based on layer-by-Layer Nano Self-Assembly", American Institute of Physics, Applied Physical Letters, Jan. 1, 2011, pp. 1-3.

International Search Report and Written Opinion of International Application No. PCT/US2016/049367, dated Nov. 14, 2016, 10 pp.

International Preliminary Report on Patentability from International Application No. PCT/US2016/049367, dated Sep. 8, 2017, 25 pp.

\* cited by examiner

FORMALDEHYDE GRAPHENE SENSOR

BACKGROUND

Formaldehyde is a naturally occurring volatile organic compound with the formula $CH_2O$. Formaldehyde is an important precursor in the production of many other materials and chemical compounds, such as particle board and various coatings.

Formaldehyde is toxic and recognized as a carcinogen. The United States National Institute for Occupational Safety and Health (NIOSH) considers 20 ppm formaldehyde in the atmosphere to be immediately dangerous to life and health (IDLH). The United States Occupation Safety and Health Administration has established a permissible exposure limit (PEL) for formaldehyde in the workplace at 0.75 parts formaldehyde per million parts of air (0.75 ppm) measured as an 8-hour time-weighted average (TWA). Other agencies and organizations have recommended that the acceptable level be reduced to less than about 0.10 ppm (100 ppb).

An excellent review of the various formaldehyde gas sensors developed over the years is provided in Chung, P.; Tzeng, C.; Ke, M.; Lee, C., Formaldehyde Gas Sensors: A Review, *Sensors*, 2013, 13, 4468-4484. Such sensors, while generally effective for measuring formaldehyde concentrations in air, tend to lack the necessary sensitivity and/or are far too expensive for widespread use. Accordingly, a substantial need exists for an economical yet robust and highly sensitive formaldehyde sensor capable of providing a quick response.

SUMMARY OF THE INVENTION

A first aspect of the invention is a formaldehyde sensitive assembly suitable for use in the manufacture of a formaldehyde electrochemical sensor. The assembly includes formaldehyde dehydrogenase attached to graphene.

A second aspect of the invention is a formaldehyde electrochemical sensor. The sensor has a formaldehyde interactive material located between and in electrical communication with a working electrode and a counter electrode. The formaldehyde interactive material includes a layer of graphene at least partially coated with immobilized formaldehyde dehydrogenase which is in fluid communication with a source of nicotinamide adenine dinucleotide.

The formaldehyde electrochemical sensor is preferably supported upon a structural substrate, and preferably also includes measurement circuitry in electrical communication with the working and counter electrodes operable for detecting the presence of any formaldehyde in fluid communication with the formaldehyde interactive material and generating an electrical signal representative of the amount of detected formaldehyde.

A third aspect of the invention is a method of measuring formaldehyde concentration within a sample. A first embodiment of the third aspect includes at least the steps of (i) obtaining a formaldehyde electrochemical sensor in accordance with the second aspect of the invention, (ii) placing the sensor into sensible fluid communication with the sample, and (iii) ascertaining a formaldehyde concentration within the sample by detecting the presence of any formaldehyde in the sample with the formaldehyde electrochemical sensor, generating an electrical signal representative of the amount of formaldehyde detected in the sample, and converting the electrical signal to a formaldehyde concentration based upon a known conversion algorithm.

A second embodiment of the third aspect includes at least the steps of (i) applying a voltage to a working electrode of a formaldehyde electrochemical sensor, the formaldehyde electrochemical sensor comprising at least (−) a working electrode and a counter electrode, (−) a formaldehyde interactive material comprising at least a layer of graphene at least partially coated with immobilized formaldehyde dehydrogenase, located between and in electrical communication with the working and counter electrodes, (−) a source of nicotinamide adenine dinucleotide in fluid communication with the formaldehyde interactive material, and (−) measurement circuitry in electrical communication with the working and counter electrodes operable for detecting the presence of any formaldehyde in fluid communication with the formaldehyde interactive material and generating an electrical signal representative of the amount of detected formaldehyde, (ii) measuring an electrical signal generated by the electrodes with the formaldehyde interactive material in sensing communication with the sample, and (iii) determining a formaldehyde concentration within the sample by converting the electrical signal to a formaldehyde concentration based upon a known conversion algorithm.

DETAILED DESCRIPTION OF A PREFERRED EMBODIMENT

Definitions
Nomenclature

| REFERENCE NO. | NAME |
|---|---|
| 100 | Formaldehyde Electrochemical Sensor |
| 110 | Structural Substrate/Wafer |
| 120 | Formaldehyde Sensitive Assembly/Formaldehyde Interactive Material |
| 122 | Graphene |
| 124 | Polymeric Electrolyte Linking Agent |
| 126 | Formaldehyde Dehydrogenase (FALDH) |
| 130 | Dielectric Material |
| 140 | Source of Nicotinamide Adenine Dinucleotide (NDA$^+$) |
| 150 | Electrodes |
| 150' | Electrical Leads |
| 151 | Working Electrode |
| 151' | Electrical Lead for Working Electrode |
| 152 | Counter Electrode |
| 152' | Electrical Lead for Counter Electrode |
| 200 | Measurement Circuitry |
| 210 | Computer |
| F | Formaldehyde |

Construction

Figure 1:
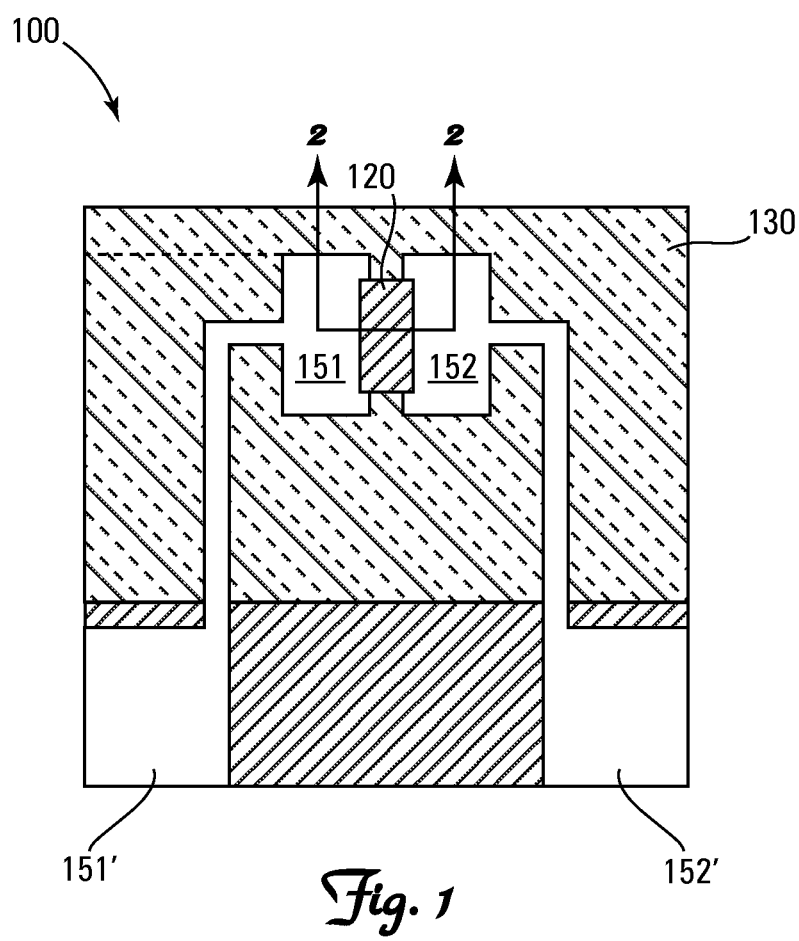
FIG. 1 is a schematic top-view of one embodiment of a formaldehyde electrochemical sensor in accordance with the second aspect of the invention.
Figure 2:
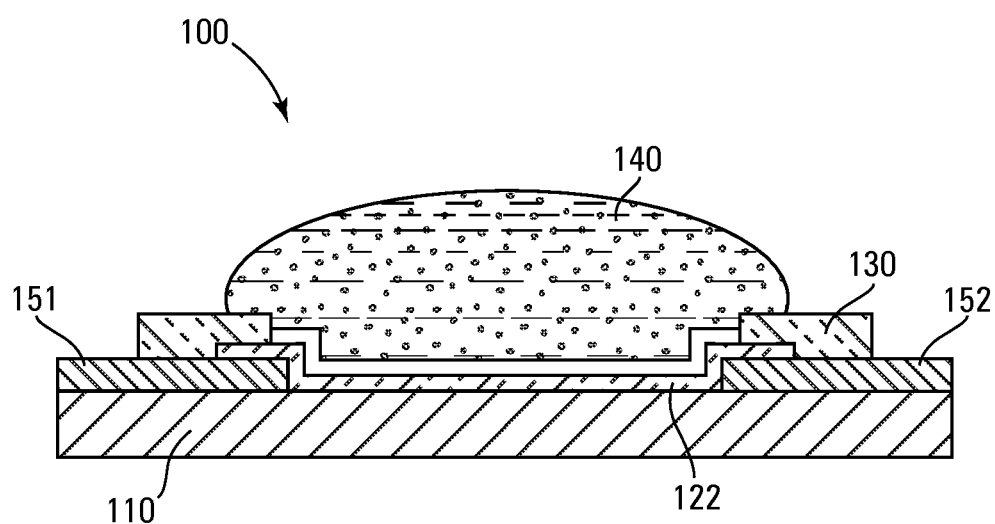
FIG. 2 is an enlarged schematic cross-section side-view of the formaldehyde interactive component of the formaldehyde electrochemical sensor depicted in FIG. 1 taken along line 2-2, and further depicting a supply of $NAD^+$ in fluid communication with the formaldehyde interactive component.

Referring to FIGS. 1 and 2, a first aspect of the invention is a formaldehyde sensitive assembly or formaldehyde interactive material 120, suitable for use in the manufacture of a formaldehyde electrochemical sensor 100. The assembly 120 includes a formaldehyde dehydrogenase (FALDH) 126 attached to graphene 122.

Formaldehyde dehydrogenase (FALDH) is an enzyme that catalyzes the chemical reaction $$CH_2O + NAD^+ + H_2O \rightleftharpoons HCOOH + NADH + H^+$$

FALDH is commercially available from a number of sources, including specifically but not exclusively, Cayman Chemical of Ann Arbor, Mich., Sigma-Aldrich of St. Louis, Mo., and Fisher Scientific of Hampton, N.H.

The use of FALDH in combination with a source of NAD$^+$ in the construction of electrochemical formaldehyde biosensors is known. See, Marzuki, N.; Bakar, F.; Salleh, A.; Heng, L.; Yusof, N.; Siddiquee, S., Development of Electrochemical Biosensor for Formaldehyde Determination Based on Immobilized Enzyme, *Int. J. Electrochem. Sci.*, 2012, 7, 6070-6083, and Wang, M.; Jiang, S.; Chen, Y.; Chen, X.; Zhao, L.; Zhang, J.; Xu, J, Formaldehyde Biosensor with Formaldehyde Dehydrogenase Adsorbed on Carbon Electrode Modified with Polypyrrole and Carbon Nanotube, *Engineering*, 2012, 5, 135-138. Both publications are incorporated herein by reference.

Graphene is fundamentally a single layer of sp2 bonded carbon atoms arranged in a honeycomb (hexagonal) lattice. Graphene is the strongest material ever recorded, more than three hundred times stronger than structural steel and more than forty times stronger than diamond. Graphene provides superior levels of electronic conduction due to its single layer structure and the occurrence of a free pi ($\pi$) electron for each carbon atom in the lattice.

There are a number of ways to produce graphene, including specifically but not exclusively, mechanical exfoliation (the adhesive tape technique), chemical vapor deposition (CVD), thermolytic growth from a solid carbon source, sonication, carbon dioxide reduction, and graphite oxide reduction. Chemical vapor deposition is the generally preferred technique.

The FALDH 126 is immobilized upon the graphene 122, preferably via a linking agent 124. The linking agent 124 is preferably a polymeric electrolyte linking agent, such as polydiallyldimethylammonium chloride (PDDA), for facilitating transport of the electron signal resulting from the chemical reaction catalyzed by FALDH 126 to the graphene 122. Other linking agents may also be employed, such as poly(allylamine hydrochloride, but we have found positively charged PDDA, self-assembled layer-by-layer (LbL) in alternating layers with negatively charged poly(sodium styrene sulfonate) (PSS) to provide an acceptable combination of retention strength and electron transport. We found poly-L-Lysine to be effective for immobilizing FALDH onto graphene, but ineffective for purposes of the invention as the resultant assembly was generally nonresponsive to formaldehyde.

Figure 3:
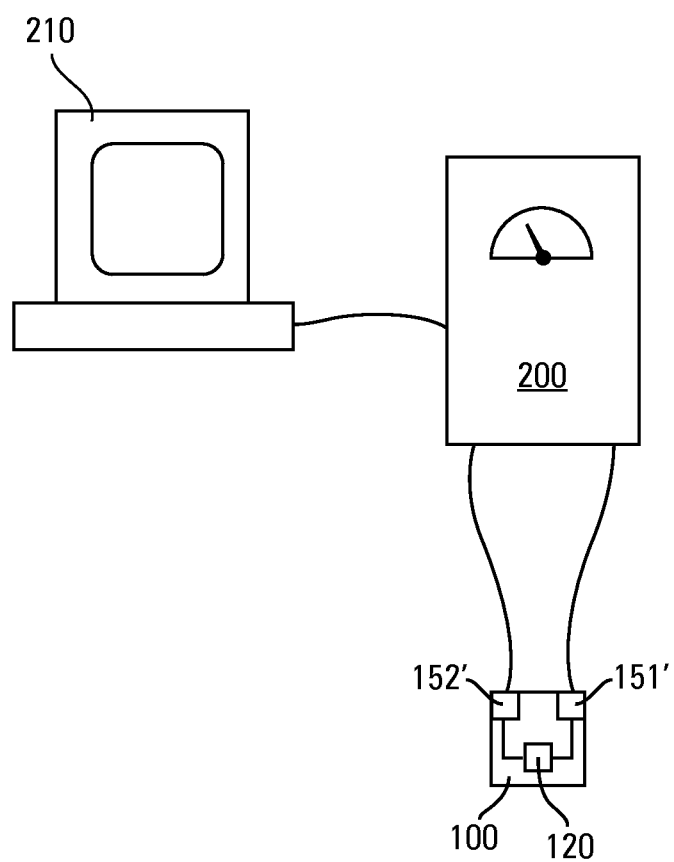
FIG. 3 is a schematic representations of a formaldehyde electrochemical sensor in accordance with the second aspect of the invention connected to measurement circuitry.
Figure 4A:
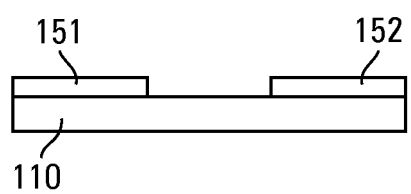
FIGS. 4A-D are schematic representations of an exemplary method of fabricating a formaldehyde electrochemical sensor in accordance with the second aspect of the invention.
Figure 4B:
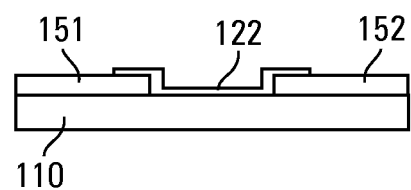
Figure 4C:
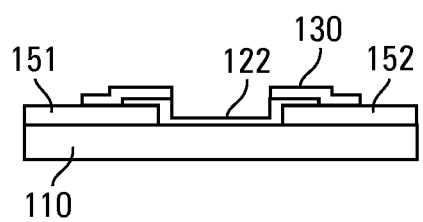
Figure 4D:
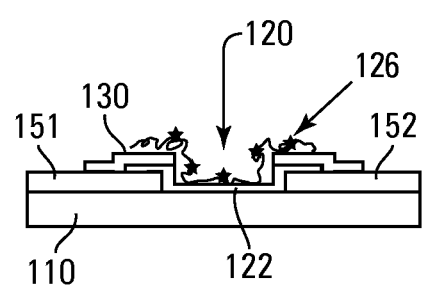
Figure 5:
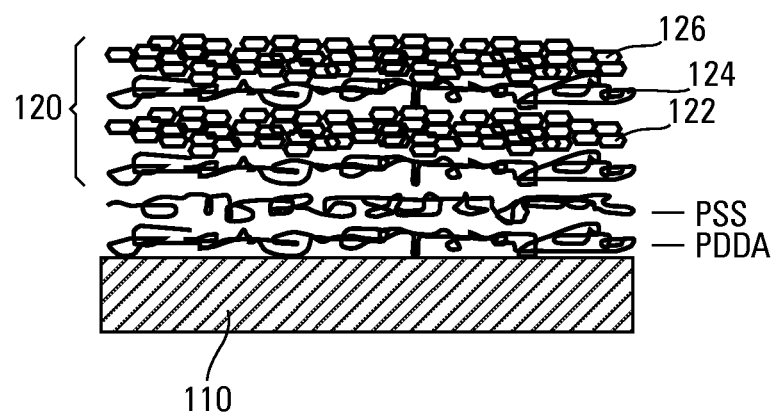
FIG. 5 is a grossly enlarged schematic representation of an exemplary formaldehyde sensitive assembly in accordance with the first aspect of the invention, secured to a structural substrate by alternating layers of positively charged polydiallyldimethylammonium chloride (PDDA) and negatively charged poly(sodium styrene sulfonate) (PSS).

Referring to FIGS. 1 and 3, a second aspect of the invention is a formaldehyde electrochemical sensor 100 employing the formaldehyde sensitive assembly 120 of the first aspect of the invention. The formaldehyde sensitive assembly 120 is positioned between and in electrical communication with a working electrode 151 and a counter electrode 152 (collectively referenced as electrodes 150). The electrodes 150 are preferably Au/Cr electrodes. The formaldehyde sensitive assembly 120 is in fluid communication with a source of the coenzyme nicotinamide adenine dinucleotide (NAD) 140, as a necessary reactant in the FALDH catalyzed chemical reaction $$CH_2O + NAD^+ + H_2O \rightleftharpoons HCOOH + NADH + H^+$$

The source of NAD$^+$ is preferably an aqueous phosphate buffered saline solution of $\beta$-NAD$^+$.

The sensor 100 preferably includes a structural substrate 110 to support the formaldehyde sensitive assembly 120 and electrodes 150, such as a wafer used in fabrication of the sensor 100.

Referring to FIGS. 1 and 2, a dielectric material 130, such as KMPR, is used as necessary to electrically insulate and isolate various components of the sensor 100 from one another.

The sensor 100 can be sized as desired for each particular application, with a general preference for a sensor 100 between about 10 to 20 mm wide, 10 to 20 mm long and a height as minimally necessary to house the required supply of NAD$^+$ atop the formaldehyde sensitive assembly 120, typically 5 to 20 mm.

Referring to FIG. 3, the electrodes 150 can be placed into electrical communication with standard measurement circuitry 200 via electrical leads 151' and 152' for detecting and measuring any electrical signal generated by the oxidation of any formaldehyde F in fluid communication with the formaldehyde interactive material 120, and generating an electrical signal representative of the amount of detected formaldehyde F. An exemplary measurement circuitry 200 suitable for use in the present invention is the 34970A data acquisition resistance analyzer available from Agilent Technologies, Inc. of Santa Clara, Calif. The generated electrical signal is then converted, typically via a software program running on a general purpose computer 210 in communication with the analyzer, to a formaldehyde concentration based upon an empirically derived conversion algorithm.

Referring to FIGS. 4A-D, a preferred method of fabricating the formaldehyde sensitive assembly 120 involves the steps of photolithographic formation of working 151 and counter 152 electrodes (collectively electrodes 150) (e.g., Cr/50 nm+Au/100 nm) on a structural substrate 110 (e.g., 300 nm SiO$_2$), (–) photolithographic formation of an LbL self-assembled layer of graphene 122 between and in electrical communication with both of the electrodes 150 (e.g., [PDDA (10 min)+PSS (10 min)]2+[PDDA (10 min)+graphene (20 min)]$_5$, (–) photolithographic formation of a dielectric coating (e.g., KMPR) as necessary and appropriate to prevent short circuiting between the electrodes 150 while leaving an area of the graphene layer 122 exposed, and (–) formation of an LbL layer of immobilized enzyme on the exposed area of the graphene layer 122 (e.g., [PDDA (10 min)+FALDH (20 min)]$_2$. Referring to FIG. 2, construction of the electrochemical sensor 100 is completed by placing a supply of NAD$^+$ in fluid communication with the enzyme coated exposed area of the graphene layer 122 (e.g., a reservoir containing an aqueous phosphate buffered saline solution of β-NAD$^+$).

EXPERIMENTAL

Experiment One

Sensor Fabrication

Thirty sensors, each approximately 10 mm by 13 mm and having the layout set forth in FIG. 1, were formed on a single 4 in diameter 300 nm thick SiO$_2$ wafer.

A 50 nm layer of Chromium and a 100 nm layer of Gold (Cr/Au) were sputter coated onto a major surface of the wafer and patterned by photolithography using Microposit S1813 as the photoresist and wet chemical etching, to form the electrodes 150 and electrical leads 150' as depicted in FIG. 1, for each of the thirty sensors.

A layer of LbL self-assembled graphene was then formed over the wafer [PDDA (10 min)+PSS (10 min)]$_2$+[PDDA (10 min)+graphene (20 min)]$_5$ and patterned by photolithography using Microposit S1813 as the photoresist and oxygen plasma etching, to form the graphene layer 122 of the formaldehyde sensitive assembly 120 as depicted in FIG. 1, for each of the thirty sensors.

A coating of KMPR was then placed over the wafer and patterned by photolithography using wet chemical etching, to form the dielectric protective coating 130 as depicted in FIG. 1 (noting removal of dielectric coating over electrodes to facilitate viewing of internal components) and FIG. 2, for each of the thirty sensors.

An incomplete layer of formaldehyde dehydrogenase (FALDH) was then immobilized onto the exposed area of the graphene layer 122 using polydiallyldimethylammonium chloride (PDDA) as the linking agent ([PDDA (10 min)+FALDH (20 min)]$_2$).

Each sensor was then stamped out from the wafer.

Experiment Two

Sensing of Formaldehyde in Aqueous Solution

A silicone o-ring was sealing secured with silicone rubber around the formaldehyde sensitive assembly of a sensor constructed in Experiment One so as to form a reservoir directly over the formaldehyde sensitive assembly of the sensor. A 20 μl volume of phosphate buffered saline solution of β-NAD$^+$ at pH 8.0, N7004 purchased from Sigma-Aldrich, was placed into the reservoir into direct fluid communication with the formaldehyde sensitive assembly.

A 34970A data acquisition resistance analyzer purchased from Agilent Technologies, Inc., connected to a general purpose computer, was electrically connected to the electrical leads on the sensor for detecting and measuring shifts in resistance [kΩ] at the sensor.

Figure 6:
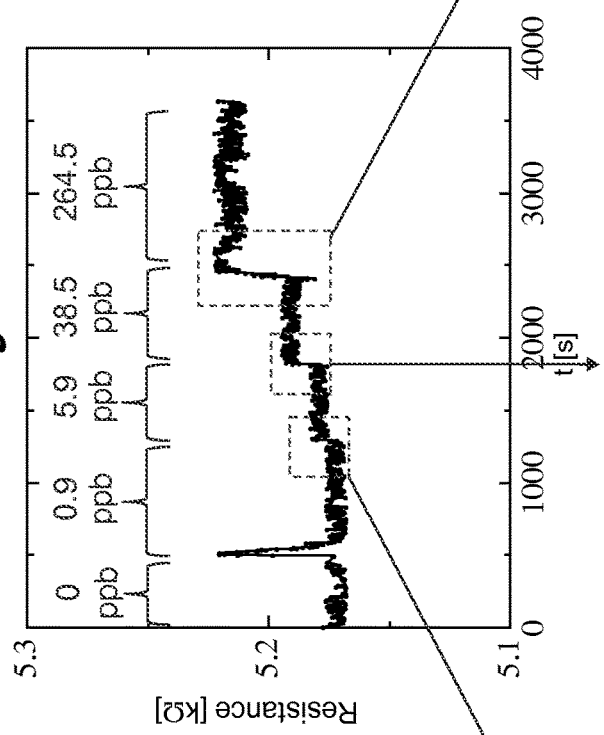
FIG. 6, is a graph depicting changes in resistance over time measured in Experiment Two.

The phosphate buffered saline solution of β-NAD$^+$ in the reservoir was sequentially injected with 20 μl of 0.006 mM, 0.06 mM, 0.6 mM and 6 mM solutions of formaldehyde over time as set forth in FIG. 6 to form samples containing the equivalent of a gas phase concentration of 0.9 ppb, 5.9 ppb, 38.5 ppb and 264.5 ppb formaldehyde based upon the transformation algorithms established by S. Dong and P. K. Dasgupta, *Environmental Science and Technology* 20 (1986), 637-640) set forth below, and shifts in resistance measured over time as displayed in FIG. 6.

$$[CH_2O(aq)] = 16650[CH_2O(g)]^{1.0789}$$

$$\log[CH_2O(g)] = ((0.9261)(\log(x_{CH2O(aq)}) - 2.2942) \pm 0.0332$$

Figure 6C:
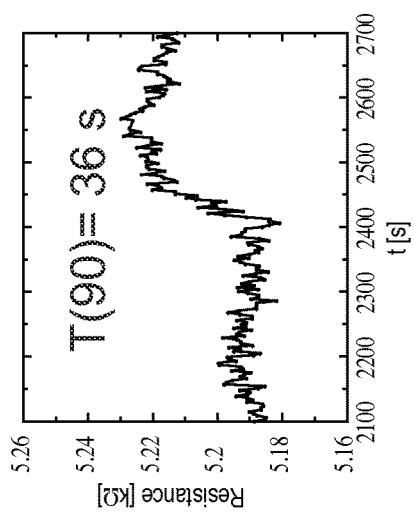
FIGS. 6A, 6B and 6C are enlarged portions of the graph depicted in FIG. 6 encompassing each measurable shift in resistance.
Figure 6B:
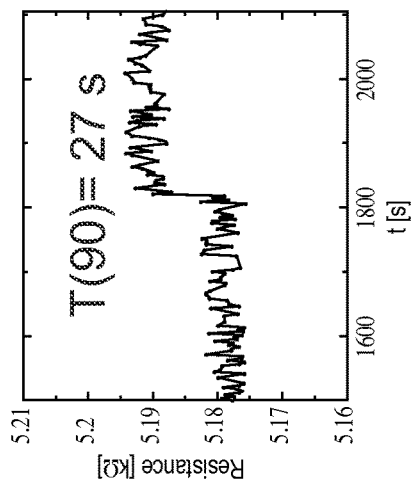
Figure 6A:
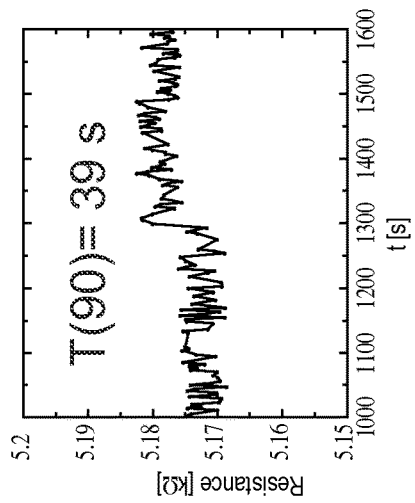

The sensor was capable of detecting formaldehyde as low as a converted concentration of 5.9 ppb as shown in FIG. 6, with a T(90) response time (i.e., the time to reach 90% of the final value) averaging 31.5 sec as depicted in FIGS. 6A, 6B and 6C.

Experiment Three

Sensing of Formaldehyde in Gas

A silicone o-ring was sealing secured with silicone rubber around the formaldehyde sensitive assembly of a sensor constructed in Experiment One so as to form a reservoir directly over the formaldehyde sensitive assembly of the sensor. An aqueous phosphate buffered saline solution of β-NAD$^+$, N7004 purchased from Sigma-Aldrich, was placed into the reservoir into direct fluid communication with the formaldehyde sensitive assembly.

A 34970A data acquisition resistance analyzer purchased from Agilent Technologies, Inc., connected to a general purpose computer, was electrically connected to the electrical leads on the sensor for detecting and measuring shifts in resistance [kΩ] at the sensor.

Figure 7A:
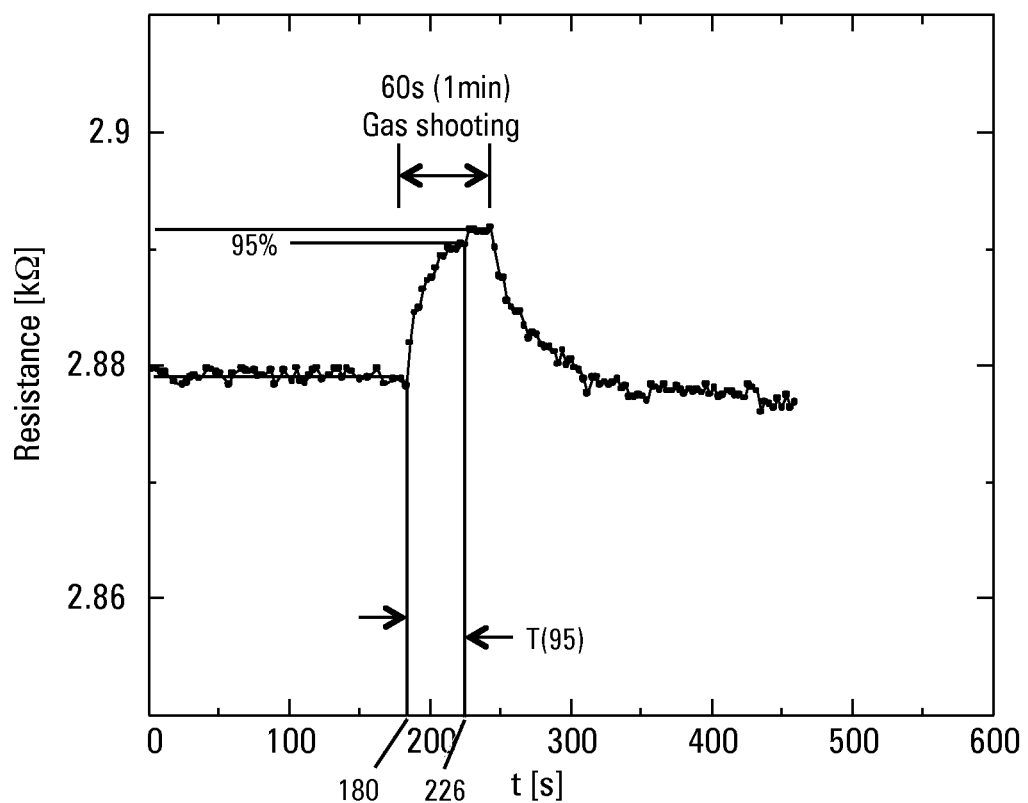
FIGS. 7A and 7B are graphs depicting changes in resistance over time measured in Experiment Three for gaseous test samples containing 1 and 2 ppm formaldehyde respectively.
Figure 7B:
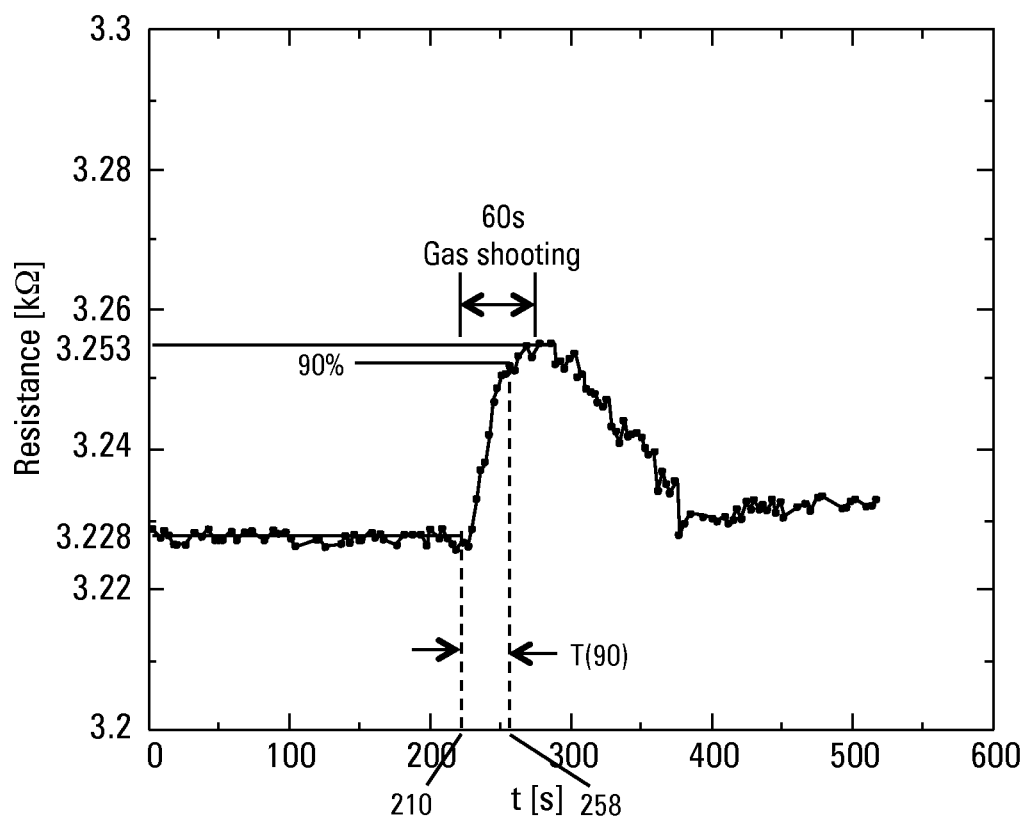

The reservoir on the sensor was covered with a polytetrafluorethylene (PTFE) membrane to reduce evaporation of the aqueous phosphate buffered saline solution of β-NAD$^+$ retained within the reservoir. Carrier gas samples of N$_2$ heated to approximately 60° C. and containing 1 ppm and 2 ppm formaldehyde, formed using a model 8990 Permeation Calibrator from Mocon, Inc. of Minneapolis, Minn. and a formaldehyde containing Trace Source™ Permeation Tube from Kin-Tek Labratories, Inc. of La Marque, Tex., were separately passed over the PTFE membrane at a flow rate of approximately 760 cm$^3$/min for 60 seconds. Shifts in resistance measured over time for each sample as the sample was passed over the PTFE membrane are displayed in FIGS. 7A and 7B.

Figure 7C:
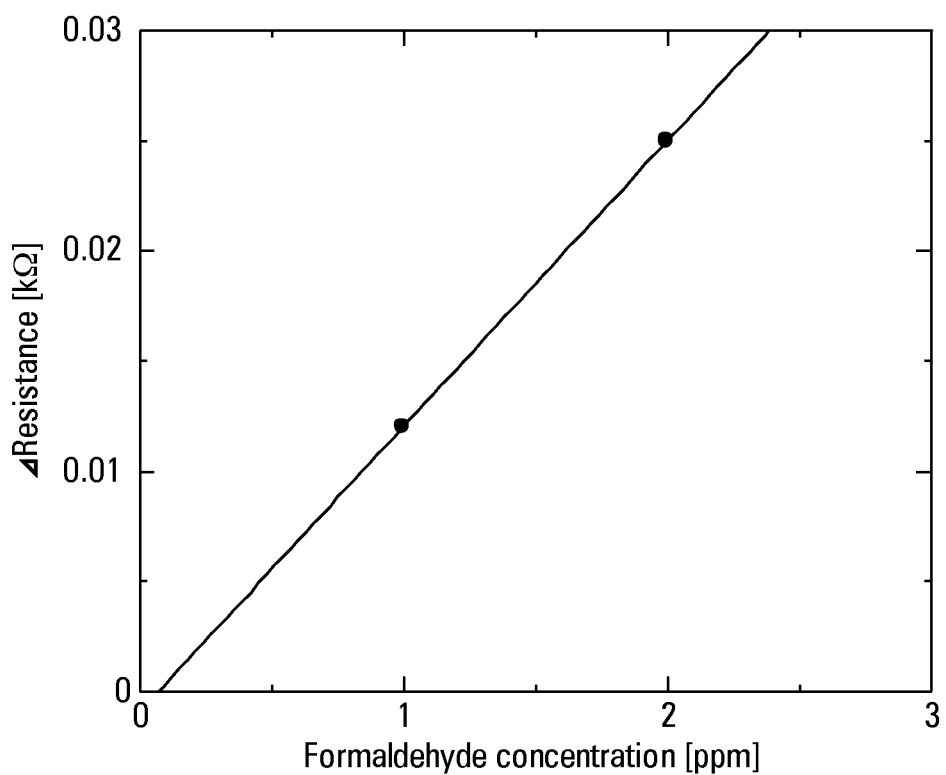
FIG. 7C is a graph of shift in resistance v. formaldehyde concentration for the two test samples measured in Experiment Three, from which an algorithm for converting the electrical signal generated by the sensor to a formaldehyde concentration can be derived.

The sensor detected a 12 ohm shift in resistance with a T(95) of 46 seconds at a formaldehyde concentration of 1 ppm in the gas sample, and a 25 ohm shift in resistance with a T(95) of 48 seconds at a formaldehyde concentration of 2 ppm in the gas sample. FIG. 7C is a graph of shift in resistance v. formaldehyde concentration for these two test samples, from which an algorithm for converting the electrical signal generated by the sensor to a formaldehyde concentration can be derived.

We claim:

1. A formaldehyde sensitive assembly suitable for use in the manufacture of a formaldehyde electrochemical sensor, comprising formaldehyde dehydrogenase attached to a single layer sheet of graphene.

2. The formaldehyde sensitive assembly of claim 1 wherein the formaldehyde dehydrogenase is attached to the graphene by a polymeric electrolyte linking agent.

3. The formaldehyde sensitive assembly of claim 2 wherein the polymeric electrolyte linking agent is polydiallyldimethylammonium chloride.

4. A formaldehyde electrochemical sensor having a formaldehyde interactive material located between and in electrical communication with a working electrode and a counter electrode, the formaldehyde interactive material comprising a single sheet of graphene at least partially coated with immobilized formaldehyde dehydrogenase which is in fluid communication with a source of nicotinamide adenine dinucleotide.

5. The formaldehyde electrochemical sensor of claim 4 further comprising measurement circuitry in electrical communication with the working and counter electrodes operable for detecting the presence of any formaldehyde in fluid communication with the formaldehyde interactive material and generating an electrical signal representative of the amount of detected formaldehyde.

6. The formaldehyde electrochemical sensor of claim 5 wherein the measured electrical property is a shift in resistance.

7. The formaldehyde electrochemical sensor of claim 4 wherein the sensor is supported upon a major surface of a structural substrate.

8. The formaldehyde electrochemical sensor of claim 7 wherein the structural substrate is a wafer.

9. The formaldehyde electrochemical sensor of claim 4 wherein the formaldehyde dehydrogenase is immobilized upon the layer of graphene by a polymeric electrolyte linking agent.

10. The formaldehyde electrochemical sensor of claim 9 wherein the polymeric electrolyte linking agent is polydiallyldimethylammonium chloride.

11. The formaldehyde electrochemical sensor of claim 4 wherein the source of nicotinamide adenine dinucleotide is an aqueous buffered solution of β-NAD$^+$.

12. The formaldehyde electrochemical sensor of claim 11 wherein the aqueous buffered solution of nicotinamide adenine dinucleotide is a phosphate buffered saline solution of nicotinamide adenine dinucleotide.

13. The formaldehyde electrochemical sensor of claim 4 wherein the graphene layer is layer-by-layer self-assembled on a wafer.

14. The formaldehyde electrochemical sensor of claim 9 wherein the polymeric electrolyte linking agent and the formaldehyde dehydrogenase are assembled layer-by-layer on the layer of graphene.

15. A method of measuring formaldehyde concentration within a sample, comprising the steps of:
    (a) obtaining a formaldehyde electrochemical sensor in accordance with claim 5,
    (b) placing the formaldehyde electrochemical sensor into sensible fluid communication with the sample, and
    (c) ascertaining a formaldehyde concentration within the sample by detecting the presence of any formaldehyde in the sample with the formaldehyde electrochemical sensor, generating an electrical signal representative of the amount of formaldehyde detected in the sample, and converting the electrical signal to a formaldehyde concentration based upon a known conversion algorithm.

16. The method of claim 15 wherein the sample is a gaseous sample.

17. A method of measuring formaldehyde concentration within a sample, comprising the steps of:
    (a) applying a voltage to a working electrode of a formaldehyde electrochemical sensor, the formaldehyde electrochemical sensor comprising at least:
        (i) a working electrode and a counter electrode,
        (ii) a formaldehyde interactive material comprising at least a single sheet of graphene at least partially coated with immobilized formaldehyde dehydrogenase, located between and in electrical communication with the working and counter electrodes,
        (iii) a source of nicotinamide adenine dinucleotide in fluid communication with the formaldehyde interactive material, and
        (iv) measurement circuitry in electrical communication with the working and counter electrodes operable for detecting the presence of any formaldehyde in fluid communication with the formaldehyde interactive material and generating an electrical signal representative of the amount of detected formaldehyde,
    (b) measuring an electrical signal generated by the electrodes with the formaldehyde interactive material in sensing communication with the sample, and
    (c) determining a formaldehyde concentration within the sample by converting the electrical signal to a formaldehyde concentration based upon a known conversion algorithm.

18. The method of claim 17 wherein the sample is a gaseous sample.

* * * * *